United States Patent [19]
Collins et al.

[11] Patent Number: 5,866,635
[45] Date of Patent: Feb. 2, 1999

[54] UV-ABSORBING BENZOTRIAZOLES HAVING A STYRENE GROUP

[75] Inventors: Theresa A. Collins, Park Ridge, Ill.; John T. Mulvihill, Collon, Ireland

[73] Assignee: Wesley Jessen Corporation, Des Plaines, Ill.

[21] Appl. No.: 18,833

[22] Filed: Feb. 4, 1998

Related U.S. Application Data

[62] Division of Ser. No. 757,807, Nov. 27, 1996, Pat. No. 5,729,322, which is a division of Ser. No. 535,086, filed as PCT/US94/04296 Apr. 22, 1994, published as WO94/24112 Oct. 27, 1994, Pat. No. 5,637,726, which is a continuation-in-part of Ser. No. 52,020, Apr. 22, 1993, abandoned.

[51] Int. Cl.$^6$ .............................. G21K 1/10; G02C 7/04; A61F 2/16; C02C 7/10; C07D 249/20; C08G 73/06

[52] U.S. Cl. .................... 523/137; 523/108; 525/258; 525/328.2; 525/328.8; 525/328.9; 525/330.7; 526/259; 528/423; 548/259; 548/260; 623/6; 351/163

[58] Field of Search ..................... 523/108, 137; 525/258, 328.2, 328.9, 328.8, 330.7; 526/259; 528/423; 548/259, 260

[56] References Cited

U.S. PATENT DOCUMENTS

| | | | |
|---|---|---|---|
| Re. 33,477 | 12/1990 | Loshaek | 526/313 |
| 3,072,585 | 1/1963 | Milionis et al. | 260/22 |

(List continued on next page.)

FOREIGN PATENT DOCUMENTS

| | | |
|---|---|---|
| 343996 | 11/1989 | European Pat. Off. . |
| 2128005 | 12/1971 | Germany . |
| 41-19179 | 11/1962 | Japan . |
| 46-26860 | 8/1971 | Japan . |
| 47-29199 | 8/1972 | Japan . |
| 61-99961 | 7/1994 | Japan . |
| 960141 | 6/1964 | United Kingdom . |
| 1177797 | 1/1970 | United Kingdom . |
| 2146647 | 4/1985 | United Kingdom . |
| 2166135 | 4/1986 | United Kingdom . |

OTHER PUBLICATIONS

Belusa et al., "2-(2-Hydroxyphenyl)benzotriazoles. I. Synthesis and their ultraviolet and infrared specta," *Chem. Zvesti*, 28, 673–79 (1974).

Belusa et al., "2-(2-Hydroxyphenyl)benzotriazoles. II. Electrophilic substitution reactions on the molecule of 2-(2-hydroxy-5-methylphenyl)benzotriazole and ultraviolet spectra of the products," *Chem zvesti*, 28, 680–85 (1974).

Gordon, *Kirk–Othmer Encyclopedia of Technology*, pp. 115–122 (2$^{nd}$ed. 1970).

Dai et al., "Functional polymers. LIV. Photochemical behavior of 2(2-hydroxphenyl)2H-benzotriazole derivatives," *Polymer Bulletin*, 20, 67–74 (1988).

Jiang et al., "Functional polymers. LV. Photochemical behavior of 2(2-hydroxphenyl)2H-benzotriazole derivatives," *Polymer Bulletin*, 20, 161–168 (1988).

Li et al., "Functional Polymers. XXII. Ultraviolet Absorbers with 2(2-hydroxphenyl)2H-benzotriazole and 2-hydroxybenzophenone (or acetophenone) chromophors in the same molecule," *J. Macromol. Sci. Chem.*, A20, 309–320 (1983).

Liu et al., "Functional polymers. LIII. Photochemical behavior of 2(2-hydroxyphenyl)2H-benzoatriazole derivatives," *Polymer Bulletin*, 20, 59–66 (1988).

*Primary Examiner*—Johann Richter
*Assistant Examiner*—Jane C. Oswecki
*Attorney, Agent, or Firm*—Brinks Hofer Gilson & Lione

[57] ABSTRACT

A reactive monomer for preparing ultraviolet absorbing polymers has formula (I) wherein $R^1$ is a halogen or $C_1$–$C_6$ straight or branched chain alkoxy group; and R is a $-(CH_2)_3O-$, $-(CH_2)_2O-$, $-CH(CH_3)CH_2O-$, $-CH_2CH(CH_3)O-$, $-(CH_2)_3OCH_2-$, $-(CH_2)_2OCH_2-$, $-CH(CH_3)CH_2OCH_2-$, or $-CH_2CH(CH_3)OCH_2-$ group. The compound can be used to produce ultraviolet absorbing polymers, such as those used for ocular devices including contact and intraocular lenses.

15 Claims, 3 Drawing Sheets

U.S. PATENT DOCUMENTS

| | | | |
|---|---|---|---|
| 3,399,173 | 8/1968 | Heller et al. | 260/147 |
| 3,761,272 | 9/1973 | Mannens et al. | 96/84 R |
| 3,813,255 | 5/1974 | Mannens et al. | 117/33.3 |
| 4,380,643 | 4/1983 | Yoshida et al. | 548/260 |
| 4,504,628 | 3/1985 | Johnson | 525/278 |
| 4,508,882 | 4/1985 | Yoshida et al. | 526/259 |
| 4,528,311 | 7/1985 | Beard et al. | 524/91 |
| 4,686,268 | 8/1987 | Kang | 526/259 |
| 4,716,234 | 12/1987 | Dunks et al. | 548/259 |
| 4,719,248 | 1/1988 | Bambury et al. | 523/108 |
| 4,785,063 | 11/1988 | Slongo et al. | 526/259 |
| 4,803,254 | 2/1989 | Dunks et al. | 525/477 |
| 4,812,575 | 3/1989 | Vogl et al. | 548/260 |
| 4,845,180 | 7/1989 | Henry et al. | 528/73 |
| 4,853,478 | 8/1989 | Colvin et al. | 560/32 |
| 4,868,251 | 9/1989 | Reich et al. | 525/479 |
| 5,039,459 | 8/1991 | Kindt-Larsen et al. | 264/2.6 |
| 5,147,902 | 9/1992 | Ichikawa et al. | 523/106 |

UV-ABSORBING BENZOTRIAZOLES HAVING A STYRENE GROUP

This application is a division of U.S. application Ser. No. 08/757,807 filed Nov. 27, 1996, issued as U.S. Pat. No. 5,729,322, which is a division of U.S. application Ser. No. 08/535,086 filed, as a PCT/US94/04296 Apr. 22, 1994, published as WO94/24112 Oct. 27, 1994, issued as U.S. Pat. No. 5,637,726, which is a CIP of U.S. application Ser. No. 08/052,020 filed Apr. 22, 1993, abandoned.

INTRODUCTION TO THE INVENTION

This invention relates to compounds which can be included in polymers to impart ultraviolet absorbing properties. The invention also encompasses ocular devices which absorb ultraviolet radiation, and to their production from ultraviolet absorbing compounds, such as by copolymerizing the compounds with suitable reactive monomers.

Contact lenses containing compounds for absorbing ultraviolet (u.v.) light have been on the market for several years. Such lenses are useful to all who live in areas where bright sunlight is common. As u.v. radiation is likely to be a cause of cataracts and senile macular degeneration, everyone who wears contact lenses can benefit from the type which absorb this radiation. Younger persons, whose eye lenses transmit more ultraviolet radiation than do those of older persons, also should be concerned with providing additional protection.

Ultraviolet absorbing lenses are especially useful for those who have had the natural lens of the eye removed, since the natural lens has u.v. absorption properties that help to protect the interior of the eye. Hence, u.v. absorbing intraocular lenses are also highly desirable, since such lenses are implanted in place of the eye's natural lens.

Loshaek discovered the use of polymerizable u.v. absorbers for producing contact and intraocular lenses in the early 1970's, e.g., as shown in U.S. Pat. No. Re. 33,477. More recently, substituted 2-phenyl benzotriazole compounds having a polymerizable acrylic group have been used to produce contact lenses, e.g., as in U.S. Pat. No. 4,716,234 to Dunks et al. The u.v. absorption technology has been applied primarily to rigid, gas permeable lenses; the commercially available soft lenses typically do not contain u.v. absorbers.

The present invention is predicated on use of substituted 2-phenyl benzotriazole compounds having a styrene group to form polymers exhibiting high degrees of u.v. absorption. These u.v. absorbing compounds have several advantages in producing polymers, particularly those used for contact lenses:

(1) Lenses produced by copolymerizing the compounds have very high u.v. absorption at the lower wavelengths, i.e, from 50 to 250 nanometers.
(2) The compounds are useful for making soft lenses.
(3) Lenses containing the compounds have u.v. absorption properties closely approximating that of the natural lens of the eye.
(4) Relatively low concentrations of the compounds in the lens are required to achieve useful levels of u.v. absorption.

SUMMARY OF THE INVENTION

The invention includes compounds having the formula:

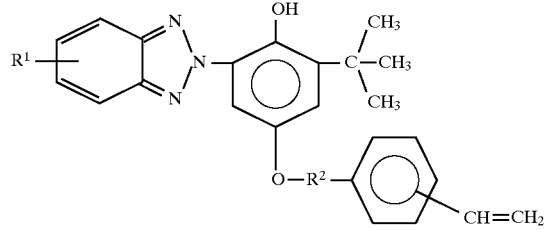

wherein $R^1$ is a halogen or $C_1$–$C_6$ straight or branched chain alkoxy group; and $R^2$ is a —$(CH_2)_3O$—, —$(CH_2)_2O$—, —$CH(CH_3)CH_2O$—, —$CH_2CH(CH_3)O$—, —$(CH_2)_3OCH_2$—, —$(CH_2)_2OCH_2$—, —$CH(CH_3)CH_2OCH_2$—, or —$CH_2CH(CH_3)OCH_2$—group.

Other aspects of the invention include polymers produced by copolymerizing the inventive compounds with one or more other monomers, polymers which include the inventive compounds in physical admixture or reacted with pendant groups, and contact and intraocular lenses made from such polymers.

DETAILED DESCRIPTION OF THE INVENTION

Figure 1:
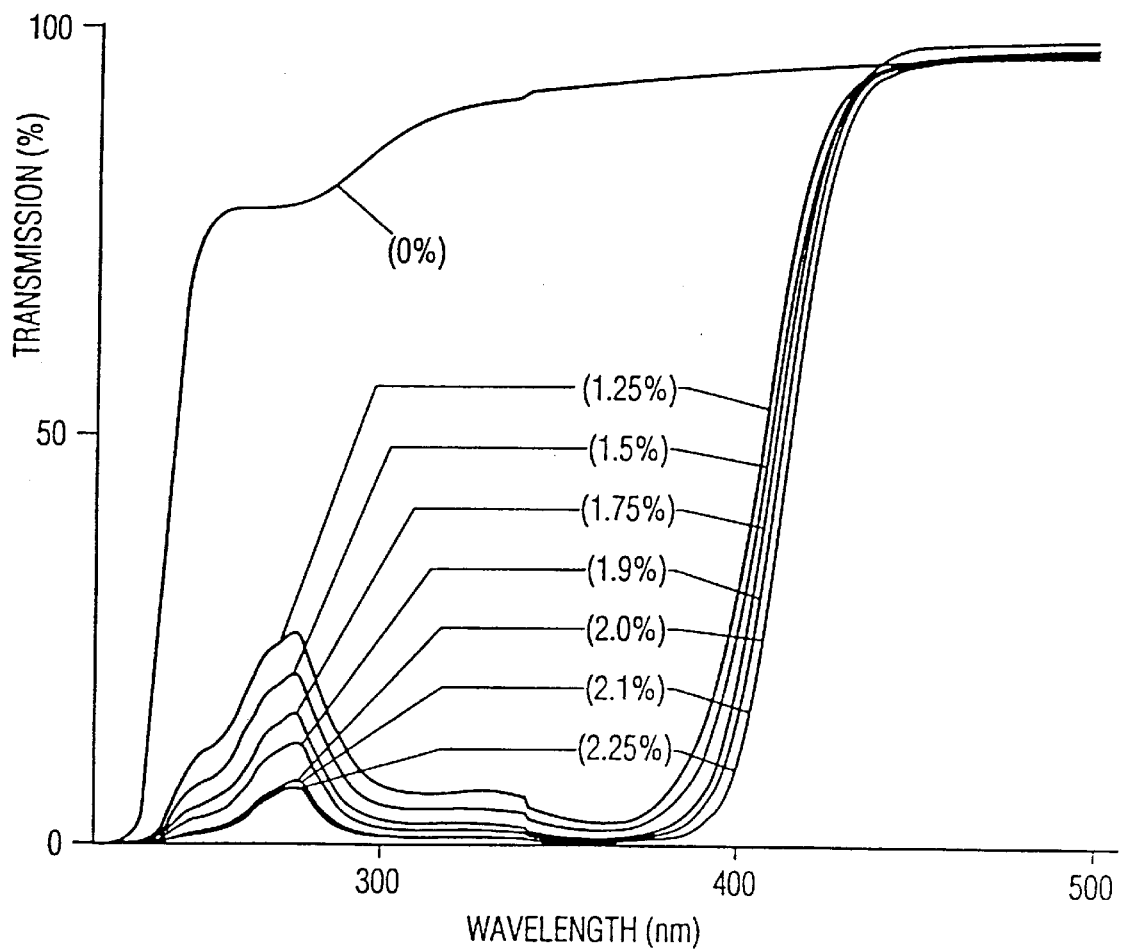
FIG. 1 is a graphical representation of the results of the experiment described in Example 3.

In the following description and claims, the term "percent" will be used to represent percentage by weight, unless the context indicates otherwise.

Ocular devices contemplated in connection with the present invention include, without limitation, windows, lenses for eyeglasses and instruments such as binoculars, goggles, face shields, contact lenses, intraocular lenses and the like. Contact lenses can include both those for correcting defective visual acuity and the so-called "bandage lenses" which are used in treating eye disorders, as well as the purely cosmetic lenses used for purposes such as changing the apparent eye color.

As noted above, the compounds of the present invention are those having the following structural formula:

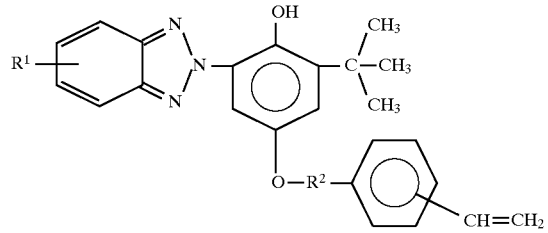

Preferred substituent groups for $R^1$ are Cl and $CH_3O$—, more preferably $CH_3O$—. The preferred substituent groups for $R^2$ are —$(CH_2)_3OCH_2$— and —$(CH_2)_2OCH_2$—, more preferably —(CH$_2$)$_3$OCH$_2$—. The more preferred compound is one wherein R$^1$ is CH$_3$O— and R$^2$ is —(CH$_2$)$_3$OCH$_2$—. A preferred structure is as follows, where the substituent groups are as described above:

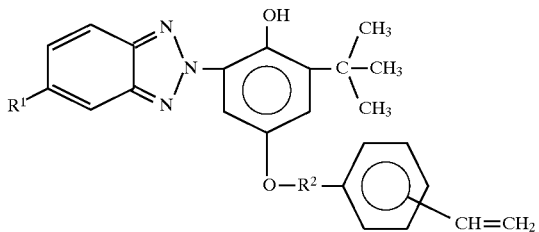

Certain preferred compounds of this invention are prepared by reacting a vinylbenzyl chloride with a 2-{2'-Hydroxy-5'-(γ-hydroxyalkoxy)-3'-t-butylphenyl}-5-(alkoxy or halo)-2H-benzotriazole having the structure:

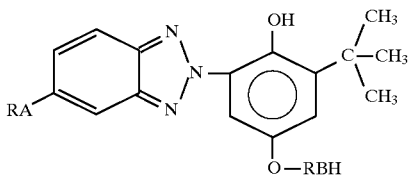

wherein R$^A$ is a halogen or C$_1$–C$_6$ straight or branched chain alkoxy group, and R$^B$ is a —(CH$_2$)$_3$O—, —(CH$_2$)$_2$O—, —CH(CH$_3$)CH$_2$O— or —CH$_2$CH(CH$_3$)O— group. The starting benzotriazole can be prepared by the method described in Examples 1–3 of U.S. Pat. No. 4,716,234 to Dunks et al., which is incorporated herein by this reference, substituting 4-halo-2-nitroaniline for the 4-methoxy-2-nitroaniline when it is desired to make R$^A$ a halogen group, and using any of 3-chloro-1-propanol, 2-chloroethanol, 2-chloro-1-propanol or 1-chloro-2-propanol to produce the desired group for R$^B$. Those skilled in the art will be aware of other groups which can be substituted for these chloro groups, such as other halogens, and for groups such as methoxy. By appropriate choice of the substituted nitroaniline, R$^A$ can be made to occupy ring positions other than that shown in the above structural formula.

The compounds of the invention can be copolymerized with a large number of unsaturated and other monomers to produce polymers having enhanced u.v. absorptive properties. Representative useful monomers include, without limitation:

(a) olefins, either straight- or branched-chain, including ethylene, propene, butenes, pentenes and the like;
(b) dienes, such as butadiene, and trienes;
(c) styrene and substituted styrenes;
(d) silanes;
(e) halogen-containing vinyl or vinylidene compounds, vinyl alcohols or esters, and the like;
(f) acrylic and methacrylic acids,,esters, amides, nitriles and the like;
(g) silicon substituted alkyl or aryl acrylic or methacrylic esters, including alkyl silicates;
(h) fluorinated alkyl or aryl substituted acrylic or methacrylic esters;
(i) vinyl pyrrolidones;
(j) vinyl silanes;
(k) vinyl sulfones;
(l) reactive mixtures of polyamines or polyhydroxy compounds and polybasic acids;
(m) epoxides, alkylene oxides or ethers;
(n) alkylidene or phenylene oxides;
(o) reactive mixtures of carboxylic or carbonic acids and polyhydroxy compounds; and
(p) reactive mixtures of isocyanates and polyhydroxy compounds.

Those skilled in the art will recognize that various of the monomers and reactive mixtures listed above, as well as others, can be copolymerized, and that the compounds of this invention can be used to form u.v. absorbing polymers with such mixtures of monomers. Copolymers which are formed can be any of random, block or grafted polymers.

In addition to incorporating the compounds into polymers by copolymerization, in many instances it is possible to form a new u.v. absorbing polymer structure by reacting the compounds with a polymerized material having pendant reactive groups, or to form a u.v. absorbing polymer by physically dispersing the compounds as additives in a formed polymer, e.g., adding a compound to a polymer melt.

Useful amounts of the compounds of the invention in a polymer range from about 0.01 percent to about 25 percent, depending upon the intended use for the polymer. In general, it will be desirable to minimize the amount of compound used, so that the physical and chemical properties of the base polymer eother than u.v. absorption) will not be significantly changed. For contact and intraocular lenses made primarily from acrylate and methacrylate polymers, about 0.05 to about 10 percent can be used, with preferred amounts being about 0.1 to about 3 percent and about 0.5 to about 1.5 percent being more preferred.

Ocular devices in accordance with the invention are produced by polymerizing a u.v. absorbing-effective amount of a compound of the above Formula I with at least one monomeric compound suitable for producing an ocular device, preferably in the case of contact and intraocular lenses hydroxyethyl methacrylate, N-vinyl pyrrolidone, alkyl methacrylates such as methyl methacrylate, aryl methacrylates, silicone methacrylate, glyceryl methacrylate, fluorinated methacrylates, alkyl substituted styrene, or combination thereof. Of course, other lens-producing monomers may be used.

Contact and intraocular lenses in accordance with invention may be hydrophilic, hard, or rigid-gas-permeable, depending on the monomer or combination thereof with which the u.v. absorbing compounds of the invention are copolymerized.

Copolymerization may take place by any of the well known methods known within the ocular device industry, e.g., by heat or u.v. light, or with a suitable initiator. Polymerization temperatures are typically 35° to 110° C., more preferably 40° to 80° C., for 5 minutes to 48 hours, more preferably 1 to 6 hours. Suitable polymerization catalysts include azobisisobutyronitrile, available from E. I. DuPont de Nemours Corporation, Wilmington, Del. U.S.A. as Vazo 64™, 2,2'-azobis (2,4-dimethylpentanenitrile), available from DuPont as Vazo 52™, and 2,5-dimethyl-2, 5-bis(2-ethylhexanoylperoxy) hexane, available from Elf-Atochem, Buffalo, N.Y. U.S.A. as Lupersol 256™.

If u.v. light is used to initiate the polymerization, its intensity should be about 0.1 to about 10 milliwatts per square contimeter, more preferably 1 to 5 mw/cm$^2$.

Lenses of the invention may be produced by first polymerizing a rod of the copolymer, cutting the rod into bonnets or buttons, and machining the bonnets or buttons into lenses, as is well known in the art. If the polymer is u.v. cured, the monomer mixture should preferably be heat cured before exposure to the u.v source. Alternatively, the lenses may be produced by any of the known molding or casting techniques, such as the methods referred to by Kindt-Larsen et al. in U.S. Pat. No. 5,039,459. The exact manner used for polymerization and lens shaping is a matter of choice and is not critical to this invention.

The following examples further describe the invention, but are not to be construed as limiting the scope of the invention.

EXAMPLE 1

A suspension of 10 grams (8.57 millimoles) of 2-{2'-Hydroxy-5'-(γ-hydroxypropoxy)-3'-t-butylphenyl}-5-methoxy-2H-benzotriazole, prepared as in U.S. Pat. No. 4,716,234, in 90 milliliters of dimethyl sulfoxide is stirred vigorously. Sodium hydride (0.49 grams, 20.5 millimoles) is added in one portion. The suspension is stirred for about 16 hours at room temperature, moisture being excluded by use of a calcium chloride trap connecting the vessel to the atmosphere. A solution of p-vinylbenzyl chloride (1.63 grams, 10.6 millimoles) and t-butylcatechol (15 milligrams) in 10 milliliters of 50 percent dimethyl sulfoxide/50 percent tetrahydrofuran is added dropwise to the suspension over about 15 minutes. Stirring is continued for about 8 hours, then the mixture is poured onto 200 milliliters of a 5 percent aqueous sodium bicarbonate solution; the pH is reduced to about 8 with 6 molar hydrochloric acid. The mixture is extracted with a total of 200 milliliters diethyl ether, the extract is washed with 200 milliliters of water and dried, then the extract is evaporated to yield a viscous oil containing about 80 to 85 percent of the compound of the following formula, where $R^2$ is —$(CH_2)_3OCH_2$—, which is used without further purification:

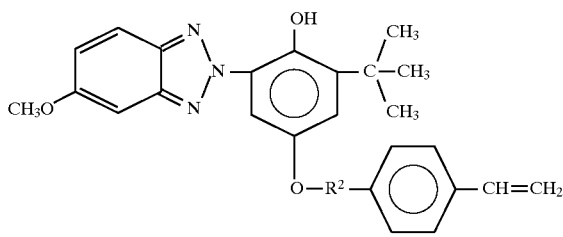

EXAMPLE 2

A glass tube, treated on its inside with a surface release agent and having an inside diameter about 15 millimeters, is charged with a polymer forming solution of 17.694 grams hydroxyethylmethacrylate, 1.567 grams ethoxyethylmethacrylate, 0.326 grams methacrylic acid, 0.023 grams of Vazo 64™, and 0.406 grams of the product of Example 1. The tube is degassed by purging with nitrogen, then the solution is allowed to cure at about 35° C. for about 24 hours, 50° C. for about 4 hours and 70° C. for about 18 hours. The glass is removed from the resulting polymer, discs 0.074 millimeters thick to simulate contact lenses are cut from the polymer rod and polished with aluminum oxide in oil, and light transmission at various wavelengths is measured.

The polymer discs are found to transmit >95 percent of the incident light intensity at 450 nm, 80 percent at 420 nm and 28 percent at 400 nm. Similar discs, from rods prepared without the Example 1 product, are found to transmit >95 percent at 450 nm, >90 percent at 420 nm and >95 percent at 400 nm.

EXAMPLE 3

Polymer discs are prepared as in Example 2, but using varying amounts of the product of Example 1. Transmission spectra are taken for each disc, and are as shown in FIG. 1.

EXAMPLE 4

Varying amounts of the product of Example 1 are dissolved in hydroxyethylmethacrylate and sufficient Vazo 64™ is added to make a 0.1 percent concentration. The solution is stirred under a pressure less than 1 torr for about 15 minutes and purged with nitrogen for an additional 15 minutes. After being transferred to a glass tube of about 15 millimeters diameter, the solution is gelled at about 35° C. for about 72 hours and cured at about 50° C. for about 4 hours and 70° C. for about 18 hours.

After removal of the glass, discs of about 1 millimeter thickness are cut from the polymer rod. The discs are hydrated for about 4 hours at about 90° C. in a borate buffer solution having a pH about 8.5 and equilibrated at room temperature for about 72 hours in an isotonic saline solution buffered at about pH 7.2. Thicknesses of the hydrated discs are between 1.056 and 1.114 millimeters.

Figure 2:
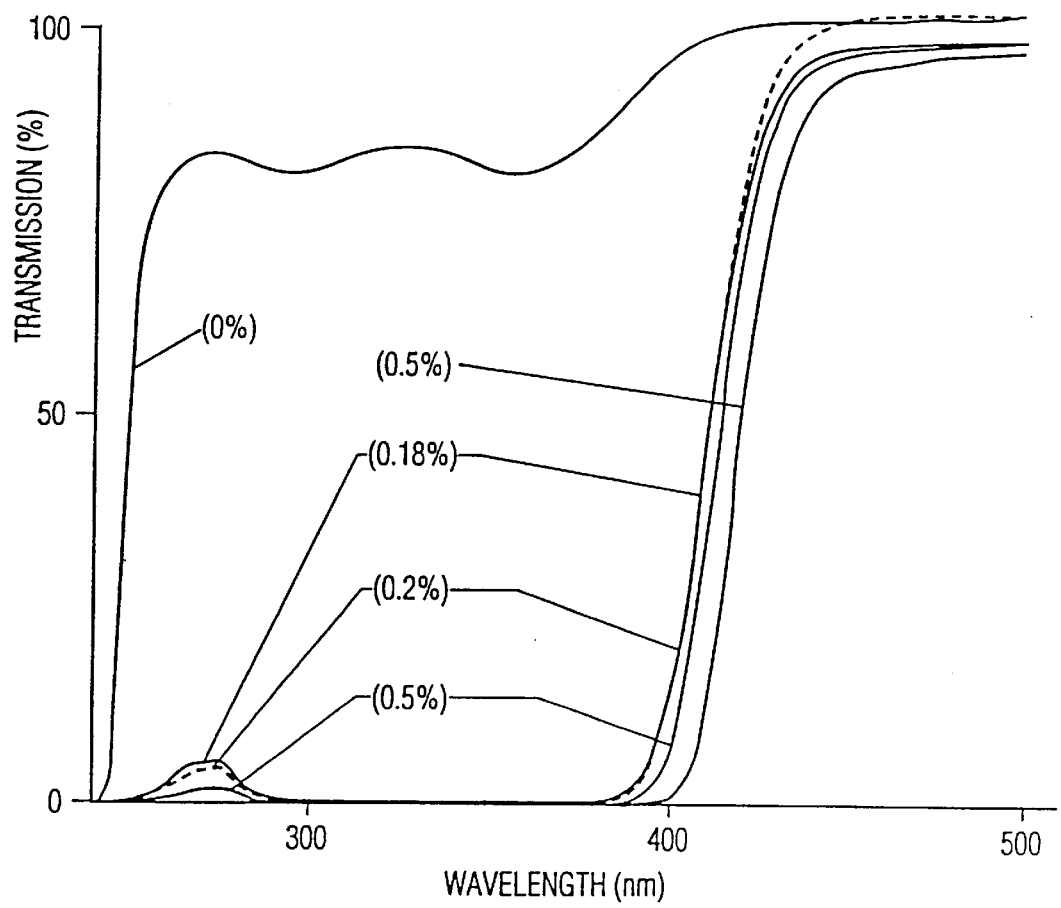
FIG. 2 is a graphical representation of the results of the experiment described in Example 4.

Transmission spectra of disks made from solutions containing varying amounts of the product of Example 1 are as shown in FIG. 2.

EXAMPLE 5

Figure 3:
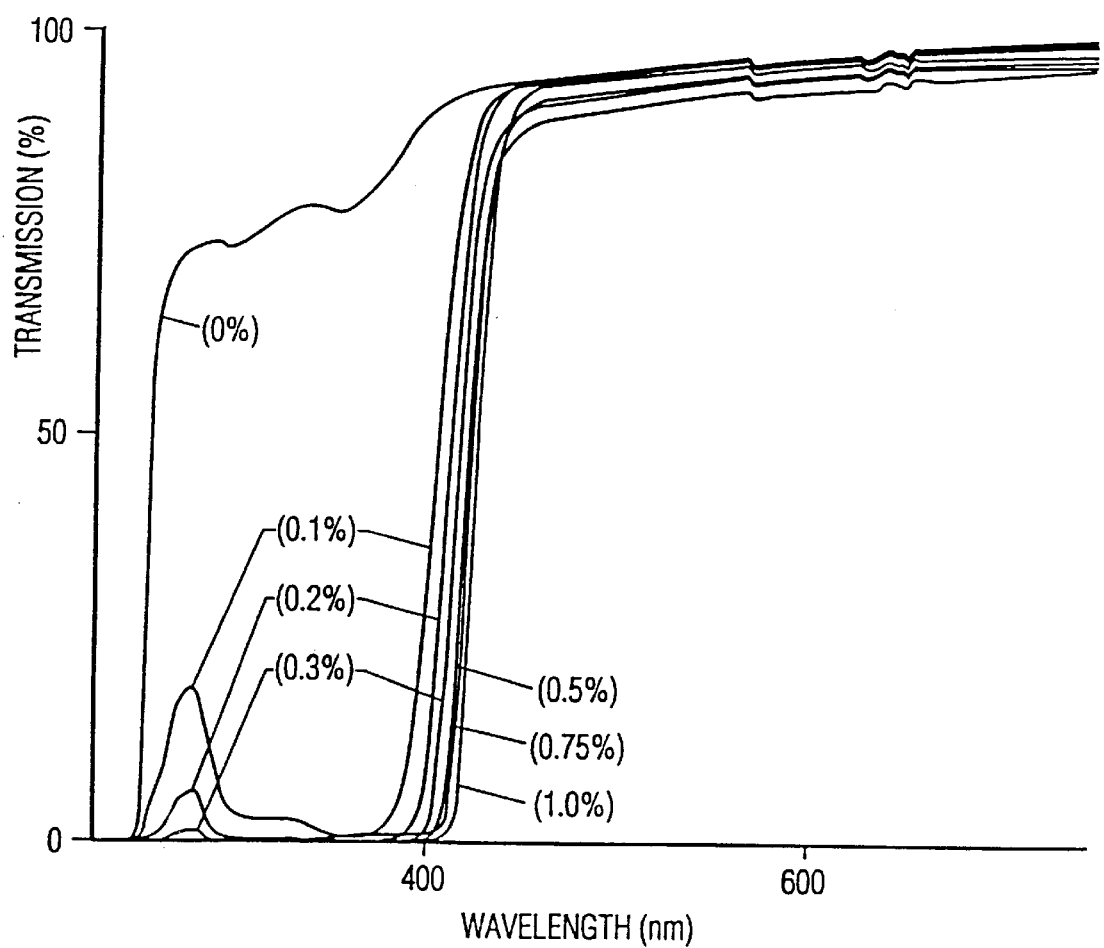
FIG. 3 is a graphical representation of the results of the experiment described in Example 5.

Polymer discs having a thickness about 1 millimeter to simulate intraocular lenses are prepared as in the preceding example, using different amounts of the compound of Example 1. Transmission spectra are as in FIG. 3.

The invention has been described with reference to specific embodiments, which are provided only for exemplification and are not to be construed as limiting the scope of the invention as defined by the appended claims.

What is claimed is:

1. A polymer which incorporates a compound having the formula:

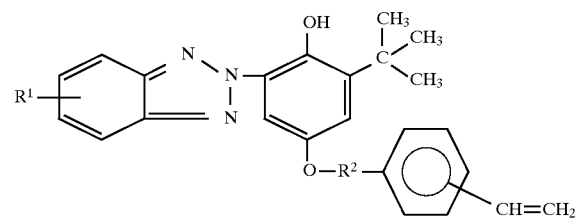

wherein $R^1$ is a halogen or $C_1$–$C_6$ straight or branched chain alkoxy group; and $R^2$ is a —$(CH_2)_3O$—, —$(CH_2)_2O$—, —$CH(CH_3)CH_2O$—, —$CH_2CH(CH_3)O$—, —$(CH_2)_3OCH_2$—, —$(CH_2)_2OCH_2$—, —$CH(CH_3)CH_2OCH_2$—, or —$CH_2CH(CH_3)OCH_2$— group, and wherein the compound is a copolymer, reacted with pendant reactive groups on the polymer or dispersed as an additive within the polymer as a melt.

2. The polymer according to claim 1 wherein $R^1$ is Cl or $CH_3O$—.

3. The polymer according to claim 1 wherein $R^1$ is $CH_3O$—.

4. The polymer according to claim 1 wherein $R^2$ is —$(CH_2)_3O$—, —$(CH_2)_2O$—, —$(CH_2)_3OCH_2$—, or —$(CH_2)_2OCH_2$—.

5. The polymer according to claim 1 wherein $R^2$ is —$(CH_2)_3OCH_2$—.

6. The polymer according to claim 1 having the formula:

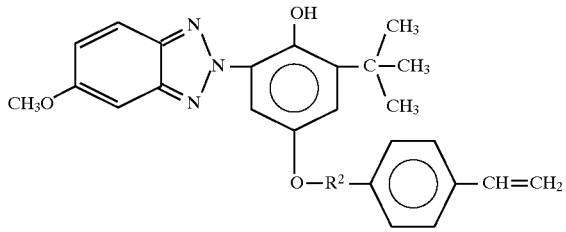

wherein $R^2$ is —$(CH_2)_3OCH_2$—.

7. The polymer of claim 1 wherein the compound of claim 1 is a comonomer.

8. The polymer of claim 7 wherein another comonomer is selected from the group consisting of olefins, dienes, styrene and substituted styrenes, silanes, vinyl or vinylidene compounds, acrylic and methacrylic compounds, silicon substituted acrylic or methacrylic compounds, vinyl pyrrolidones, reactive mixtures of polyamines or polyhydroxy compounds and polybasic acids, epoxides, ethers, alkylene oxides, phenylene oxides, reactive mixtures of carboxylic or carbonic acids and polyhydroxy compounds, and reactive mixtures of isocyanates and polyhydroxy compounds.

9. The polymer of claim 7, wherein another comonomer is selected from the group consisting of acrylates, methacrylates, vinyl pyrrolidones, and styrenes.

10. The polymer of claim 1, wherein the compound of claim 1 is reacted with a polymerized material having pendant reactive groups.

11. The polymer of claim 1, wherein the compound of claim 1 is dispersed in a formed polymer.

12. The polymer of claim 1 which incorporates about 0.01 to about 25 percent of the compound of claim 1.

13. The polymer of claim 1 which incorporates about 0.05 to about 10 percent of the compound of claim 1.

14. The polymer of claim 11 which incorporates about 0.1 to about 3 percent of the compound of claim 1.

15. The polymer of claim 11 which incorporates about 0.5 to about 1.5 percent of the compound of claim 1.

* * * * *

UNITED STATES PATENT AND TRADEMARK OFFICE
CERTIFICATE OF CORRECTION

PATENT NO. : 5,866,635
DATED : February 2, 1999
INVENTOR(S) : Theresa A. Collins et al.

It is certified that error appears in the above-identified patent and that said Letters Patent is hereby corrected as shown below:

On the Title Page

In column 2, line 3, under "ABSTRACT", change "and R" to --and $R^2$--.

In the Claims

Column 8, claim 14, line 1, change "11" to --1--.

Column 8, claim 15, line 1, change "11" to --1--.

Signed and Sealed this

Sixth Day of June, 2000

Attest:

Q. TODD DICKINSON

*Attesting Officer*    *Director of Patents and Trademarks*